United States Patent
Lakatos et al.

(10) Patent No.: US 9,697,305 B2
(45) Date of Patent: Jul. 4, 2017

(54) SYSTEMS AND METHODS FOR IDENTIFYING THERMODYNAMIC EFFECTS OF ATOMIC CHANGES TO POLYMERS

(71) Applicant: ZYMEWORKS INC., Vancouver (CA)

(72) Inventors: Gregory Lakatos, Vancouver (CA); James Liam McWhirter, Vancouver (CA)

(73) Assignee: ZYMEWORKS INC., Vancouver (CA)

( * ) Notice: Subject to any disclaimer, the term of this patent is extended or adjusted under 35 U.S.C. 154(b) by 0 days.

(21) Appl. No.: 14/775,956

(22) PCT Filed: Mar. 13, 2014

(86) PCT No.: PCT/CA2014/050240
§ 371 (c)(1),
(2) Date: Sep. 14, 2015

(87) PCT Pub. No.: WO2014/138994
PCT Pub. Date: Sep. 18, 2014

(65) Prior Publication Data
US 2016/0034616 A1 Feb. 4, 2016

Related U.S. Application Data

(60) Provisional application No. 61/793,203, filed on Mar. 15, 2013, provisional application No. 61/834,754, filed on Jun. 13, 2013.

(51) Int. Cl.
G06F 17/50 (2006.01)
G06F 19/16 (2011.01)
G06F 17/10 (2006.01)

(52) U.S. Cl.
CPC .......... G06F 17/5009 (2013.01); G06F 17/10 (2013.01); G06F 19/16 (2013.01)

(58) Field of Classification Search
USPC .................................. 703/2, 11; 702/27, 32
See application file for complete search history.

(56) References Cited

U.S. PATENT DOCUMENTS 6,178,384 B1 * 1/2001 Kolossvary ........... G06F 19/704
702/27
6,631,332 B2 10/2003 Skolnick et al.
(Continued)

OTHER PUBLICATIONS

Chin et al., 2003, Science 301, 964.
(Continued)

*Primary Examiner* — Thai Phan
(74) *Attorney, Agent, or Firm* — Morgan, Lewis & Bockius LLP; Brett Lovejoy

(57) ABSTRACT

Systems and methods for evaluating thermodynamics of atomic changes in a polymer include using a first portion of a refined derived set of three-dimensional coordinates for a derivation of the polymer, which incorporates the atomic change under study, to compute a first effective atomistic Hessian. A second effective atomistic Hessian is computed using a second portion of a refined native set of three-dimensional coordinates for the native polymer. Atoms in the first and second portions are identical. A thermodynamic property of the first portion is determined using the refined derived set of three-dimensional coordinates and the first effective atomistic Hessian. A thermodynamic property of the second portion of the native polymer is determined using the refined native set of three-dimensional coordinates and the second effective atomistic Hessian. The effect of the atomic changes is quantified by taking the difference between the calculated thermodynamic properties of the first and second portions.

27 Claims, 3 Drawing Sheets

(56) References Cited

U.S. PATENT DOCUMENTS

| | | | | |
|---|---|---|---|---|
| 7,599,059 | B2* | 10/2009 | Laurence | G01J 1/42 |
| | | | | 356/317 |
| 8,580,932 | B2* | 11/2013 | Damborsky | C07K 1/00 |
| | | | | 530/402 |
| 2005/0003389 | A1 | 1/2005 | Wang et al. | |
| 2010/0138205 | A1* | 6/2010 | Sanbonmatsu | G06F 19/16 |
| | | | | 703/12 |
| 2011/0257104 | A1* | 10/2011 | Chennamsetty | G06F 19/16 |
| | | | | 514/21.2 |
| 2013/0102763 | A1* | 4/2013 | Damborsky | C07K 1/00 |
| | | | | 530/402 |

OTHER PUBLICATIONS

Seeliger et al., "Conformational Transitions Upon Ligand Binding: Holo-Structure Prediction from Apo Conformations." PLOS Computational Biology, vol. 6, No. 1, pp. 1-9 (2010).

Stella et al., "Molecular dynamics simulations of human glutathione transferase P1-1: Analysis of the induced-fit mechanism by GSH binding." Proteins: Structure, Function, and Bioinformatics, vol. 37, No. 1, pp. 1-9 (1999).

Zheng and Brooks, "Normal-Modes-Based Prediction of Protein Conformational Changes Guided by Distance Constraints." Biophysical Journal, vol. 88, No. 5, pp. 3109-3117 (2005).

* cited by examiner

SYSTEMS AND METHODS FOR IDENTIFYING THERMODYNAMIC EFFECTS OF ATOMIC CHANGES TO POLYMERS

RELATED APPLICATIONS

This Application claims priority to U.S. Provisional Application No. 61/793,203, filed Mar. 15, 2013, and U.S. Provisional Application No. 61/834,754, filed Jun. 13, 2013, both entitled "Systems and Methods for Identifying Thermodynamic Effects of Atomic Changes to Polymers" and each of which is hereby incorporated by reference herein in its entirety.

TECHNICAL FIELD

The disclosed embodiments relate generally to systems and methods for identifying and quantifying the thermodynamic effects of atomic changes to polymers (e.g., proteins, nucleic acids, ribonucleic acids, polysaccharides, etc.).

BACKGROUND

Polymer engineering involves making mutations (atomic replacement, insertion, or deletion) in a polymer of known sequence and structure, and evaluating the effects of such mutations on the physical and biological properties of the polymer. A central approach to an understanding of the effects of a mutation is to estimate the difference in conformational flexibility between the native polymer and the derivation of the polymer (where the derivation of the polymer has the mutation) in the region near the site of the mutation.

To assist in this approach, many measures of conformational flexibility can be defined, including the root-mean square fluctuation, and the Boltzmann entropy. From a thermodynamic standpoint, the entropy provides the most natural means of quantifying the flexibility in a polymer. However, when two polymers of different primary sequence are compared, differences in the total molecular entropy may not be informative due to the different number of degrees of freedom in the two polymers. For example, consider a mutation in a protein that changes a large residue to one that is significantly smaller. The total molecular entropy of the mutated (derived) protein may be lower than the total molecular entropy of the native protein, despite an increase in the conformational freedom of the derived protein about the mutation site, simply because a small residue intrinsically has less conformational flexibility than a large residue. From an engineering standpoint however, the obvious reduction in entropy resulting from the shift from a large to a small residue is not of primary interest, while the small increase in the conformational freedom of the environment about the residue is very important.

As the above illustrates, when computing the effects of a mutation on the conformational flexibility of a polymer, there is a clear need to compensate for the size difference between mutant and wild type residues, or to separate the contributions of the mutated residue and the environment about the residue to the total entropy. Given the above background, there is a need for improved tools for studying and quantifying the thermodynamic effects of mutations in polymers.

SUMMARY

An aspect of the present disclosure combines a way of computing the local thermodynamic differences between polymers (e.g. polymers with different primary sequences), and a way of eliminating the effects of size differences between the mutant and wild type residues, in order to provide polymer engineers with a quantitative estimate of the change in the local conformational freedom of a polymer upon mutation. The disclosed methods also enable calculation of the change in conformational freedom of arbitrary subunits of a protein, which result from mutations. For example, consider the case of a protein loop and the effect mutations may have on the conformational flexibility of that loop, even in those cases where the mutations are not in the loop, or directly contacting it. The disclosed systems and methods provide a way of computing an estimate of the conformational flexibility of the loop only, and computing the differences between the loop flexibility in the mutant and native proteins, or between different mutant proteins. While the example of a protein loop is detailed above, the approach can be used to investigate changes in flexibility for any subunit, or portion thereof, of a polymer.

One aspect of the present disclosure provides a method of identifying a thermodynamic effect of an atomic replacement, insertion or deletion in a polymer. At a computer system having one or more processors and memory storing one or more programs to be executed by the one of more processors, a derived set of three-dimensional coordinates (e.g., structurally refined) $\{y_1, \ldots, y_N\}$ for a derivation of the polymer, the derivation of the polymer formed by incorporating the atomic replacement, insertion or deletion into the polymer, is used to compute a first atomistic Hessian of a first portion of the derivation of the polymer. Each respective $y_i$ in $\{y_1, \ldots, y_N\}$ is a three dimensional coordinate for an atom in a first plurality of atoms in the derivation of the polymer. Moreover, a structurally refined native set of three-dimensional coordinates $\{x_1, \ldots, x_M\}$ for the native polymer is used to compute a second atomistic Hessian of a second portion of the native polymer. Each respective $x_i$ in $\{x_1, \ldots, x_M\}$ is a three dimensional coordinate for an atom in a second plurality of atoms in the native version of the polymer. A thermodynamic property of the first portion of the derivation of the polymer is computed using the derived set of three-dimensional coordinates $\{y_1, \ldots, y_N\}$ and the first atomistic Hessian. A thermodynamic property of the second portion of the native polymer is computed using the native set of three-dimensional coordinates $\{x_1, \ldots, x_M\}$ and the second atomistic Hessian.

In some embodiments, the thermodynamic effect of the atomic replacement, insertion or deletion is quantified by taking a difference between the thermodynamic property of the first portion and the thermodynamic property of the second portion.

In some embodiments, the polymer is a protein and the atomic replacement, insertion or deletion is a mutation of one or more residues in the derivation of the polymer relative to the native polymer. In some embodiments, the polymer is a protein and the derivation of the polymer differs from the native polymer by the insertion or deletion of one or more residues at a location in the polymer.

In some embodiments, the thermodynamic property of the first portion of the derivation of the polymer is entropy, average energy, average enthalpy, free energy or heat capacity. In some embodiments, the first portion consists of those atoms in the first plurality of atoms within a distance threshold of the location of the atomic replacement, insertion or deletion.

In some embodiments, the polymer is a protein, a polypeptide, a polynucleic acid, a polyribonucleic acid, a polysaccharide, or an assembly of any combination thereof.

In some embodiments, the derived set of three-dimensional coordinates $\{y_1, \ldots, y_N\}$ for a derivation of the polymer is prepared prior to using the coordinates to compute the first atomistic Hessian by structurally refining a first refinement zone encompassing the first portion of the derivation of the polymer while holding the other portions of the derivation of the polymer fixed. Further, the native set of three-dimensional coordinates is prepared prior to using the coordinates to compute the second atomistic Hessian by structurally refining a second refinement zone encompassing the second portion of the native polymer while holding the other portions of the native polymer fixed.

In some embodiments, the derived set of three-dimensional coordinates $\{y_1, \ldots, y_N\}$ is obtained by structurally refining a first refinement zone of the derivation of the polymer, the first refinement zone encompassing the atoms in the atomic replacement, insertion or deletion. Moreover, atoms in the first refinement zone are partitioned into a first partition and a second partition. The atoms in this first partition are those atoms in the refinement zone that are in the atomic replacement, insertion or deletion. The atoms in the second partition are those atoms that are not in the first partition but are in the refinement zone. The atoms in the second partition are designated the first portion of the derivation of the polymer. For instance, if residues X and Y of the native polymer are mutated to form the derivation of the polymer, the atoms of residues X and Y form the first partition while all other atoms in the refinement zone form the second partition and the atoms in the second partition are collectively designated the first portion of the derivation of the polymer. Here, the atomic Hessian computed for the first refinement zone is decomposed using a vibrational subsystem analysis to produce a first effective Hessian matrix, and the entropy of the first portion is computed from the first effective Hessian matrix. Vibrational subsystem analysis is disclosed in Woodcock et al., 2008, "Vibrational subsystem analysis: A method for probing free energies and correlations in the harmonic limit," *J. Chem Phys.* 129, p. 214109, which is hereby incorporated by reference herein in its entirety.

In some embodiments, the derived set of three-dimensional coordinates $\{y_1, \ldots, y_N\}$ is obtained by structurally refining a first refinement zone of the derivation of the polymer. The first refinement zone encompasses the atoms in the atomic replacement, insertion or deletion. The first refinement zone is partitioned into a first partition and a second partition. The atoms in the first partition are those atoms in the first refinement zone that are in the residues participating in the atomic replacement, insertion or deletion. For instance, if residues X and Y are replaced in a native polymer in order to form the derivation of the polymer, the atoms of residues X and Y (i.e., the atoms of their counterparts in the derivation of the polymer) constitute the first partition. The atoms in the second partition are those atoms not in the first partition but that are in the first refinement zone. The atoms in the second partition are designated as the first portion of the derivation of the polymer. The native set of three-dimensional coordinates $\{x_1, \ldots, x_M\}$ is obtained by refining a second refinement zone of the native polymer. The second refinement zone corresponds to the first refinement zone but differs by those atoms participating in the atomic replacement, insertion or deletion. The second refinement zone is partitioned into a third partition and a fourth partition. The identity of the atoms in the fourth partition exactly corresponds to the identity of their counterparts in the second partition. The number of atoms in the second and fourth partitions is the same in such embodiments. The second portion of the native polymer consists of the atoms in the fourth partition. In some such embodiments, the atomistic Hessian of the first refinement zone is decomposed using a vibrational subsystem analysis to produce a first effective Hessian matrix, and the entropy of the first portion is computed from the first effective Hessian matrix. Further, the atomistic Hessian of the second refinement zone is decomposed using a vibrational subsystem analysis to produce a second effective Hessian matrix, and the entropy of the second portion is computed from the second effective Hessian matrix.

Another aspect of the present disclosure provides a method of identifying a thermodynamic effect of an atomic replacement, insertion or deletion in a polymer. At a computer system having one or more processors and memory storing one or more programs to be executed by the one of more processors, a derived set of three-dimensional coordinates (e.g., structurally refined) $\{y_1, \ldots, y_N\}$ is used for a derivation of the polymer. The derivation of the polymer is formed by incorporating the atomic replacement, insertion or deletion into the polymer. A first Hessian is then computed for all the degrees of freedom in $\{y_i, \ldots, y_N\}$. Each respective $y_i$ in $\{y_1, \ldots, y_N\}$ is a three dimensional coordinate for an atom in a first plurality of atoms in the derivation of the polymer. A native set of three-dimensional coordinates (e.g., structurally refined) $\{x_1, \ldots, x_M\}$ for the native polymer is used to compute a second atomistic Hessian for all the degrees of freedom $\{x_1, \ldots, x_M\}$ of the native polymer, where each respective $x_i$ in $\{x_1, \ldots, x_M\}$ is a three dimensional coordinate for an atom in a second plurality of atoms in the native polymer, and where an identity of at least one $y_i$ in $\{y_1, \ldots, y_N\}$ is different than an identity of the corresponding $x_i$ in $\{x_1, \ldots, x_M\}$ or N is different than M. An unnormalized thermodynamic property of the derivation of the polymer is computed using the derived set of three-dimensional coordinates and the first atomistic Hessian. An unnormalized thermodynamic property of the native polymer is computed using the native set of three-dimensional coordinates and the second atomistic Hessian. The unnormalized thermodynamic property of the derivation of the polymer and the unnormalized thermodynamic property of the native polymer are respectively normalized by taking into account a difference in a number of degrees of freedom of $\{y_1, \ldots, y_N\}$ relative to $\{x_1, \ldots, x_M\}$, thereby identifying a thermodynamic effect of the atomic replacement, insertion or deletion in the polymer.

Another aspect of the present disclosure provides a computer system for identifying a thermodynamic effect of an atomic replacement, insertion or deletion in a polymer, the computer system comprising at least one processor and memory storing at least one program for execution by the at least one processor, the memory further comprising instructions for executing any of the methods disclosed herein.

Still another aspect provides a computer system for identifying a thermodynamic effect of an atomic replacement, insertion or deletion in a polymer, the computer system comprising at least one processor and memory storing at least one program for execution by the at least one processor, the memory further comprising instructions for using a derived set of three-dimensional coordinates (e.g., structurally refined) $\{y_1, \ldots, y_N\}$ for a derivation of the polymer, the derivation of the polymer formed by incorporating the atomic replacement, insertion or deletion into the polymer, to compute a first atomistic Hessian of a first portion of the derivation of the polymer, wherein each respective $y_i$ in $\{y_1, \ldots, y_N\}$ is a three dimensional coordinate for an atom in a first plurality of atoms in the derivation of the polymer.

The memory further comprises instructions for using a native set of three-dimensional coordinates (e.g., structurally refined) $\{x_1, \ldots, x_M\}$ for the native polymer to compute a second atomistic Hessian of a second portion of the native polymer, where each respective $x_i$ in $\{x_1, \ldots, x_M\}$ is a three dimensional coordinate for an atom in a second plurality of atoms in the native version of the polymer. Optionally, an identity of each atom in the first portion of the derived set of three-dimensional coordinates $\{y_1, \ldots, y_N\}$ is identical to the corresponding atom in the second portion of the native three-dimensional coordinates $\{x_1, \ldots, x_N\}$. The memory further comprises instructions for computing a thermodynamic property of the first portion of the derivation of the polymer using the derived set of three-dimensional coordinates $\{y_1, \ldots, y_N\}$ and the first atomistic Hessian. The memory further comprises instructions for computing a thermodynamic property of the second portion of the native polymer using the native set of three-dimensional coordinates $\{x_1, \ldots, x_M\}$ and the second atomistic Hessian.

Another aspect of the present disclosure provides a non-transitory computer readable storage medium storing a computational module for identifying a thermodynamic effect of an atomic replacement, insertion or deletion in a polymer, the computational module comprising instructions for performing any of the methods disclosed herein.

Another aspect of the present disclosure provides a non-transitory computer readable storage medium storing a computational module for identifying a thermodynamic effect of an atomic replacement, insertion or deletion in a polymer, the computational module comprising instructions for using a derived set of three-dimensional coordinates (e.g., structurally refined) $\{y_1, \ldots, y_N\}$ for a derivation of the polymer, the derivation of the polymer formed by incorporating the atomic replacement, insertion or deletion into the polymer, to compute a first atomistic Hessian of a first portion of the derivation of the polymer, where each respective $y_i$ in $\{y_1, \ldots, y_N\}$ is a three dimensional coordinate for an atom in a first plurality of atoms in the derivation of the polymer. The computational module further comprises instructions for using a native set of three-dimensional coordinates (e.g., structurally refined) $\{x_1, \ldots, x_M\}$ for the native polymer to compute a second atomistic Hessian of a second portion of the native polymer. Each respective $x_i$ in $\{x_1, \ldots, x_M\}$ is a three dimensional coordinate for an atom in a second plurality of atoms in the native version of the polymer. Optionally, an identity of each atom in the first portion of the derived set of three-dimensional coordinates $\{y_1, \ldots, y_N\}$ is identical to the corresponding atom in the second portion of the native three-dimensional coordinates $\{x_1, \ldots, x_N\}$. The computational module further comprises instructions for computing a thermodynamic property of the first portion of the derivation of the polymer using the derived set of three-dimensional coordinates $\{y_1, \ldots, y_N\}$ and the first atomistic Hessian. The computational module further comprises instructions for computing a thermodynamic property of the second portion of the native polymer using the native set of three-dimensional coordinates $\{x_1, \ldots, x_M\}$ and the second atomistic Hessian.

BRIEF DESCRIPTION OF THE DRAWINGS

The embodiments disclosed herein are illustrated by way of example, and not by way of limitation, in the figures of the accompanying drawings. Like reference numerals refer to corresponding parts throughout the drawings.

DETAILED DESCRIPTION OF THE EMBODIMENTS

The embodiments described herein provide systems and methods for a thermodynamic effect of an atomic replacement, insertion or deletion in a polymer.

Figure 1:
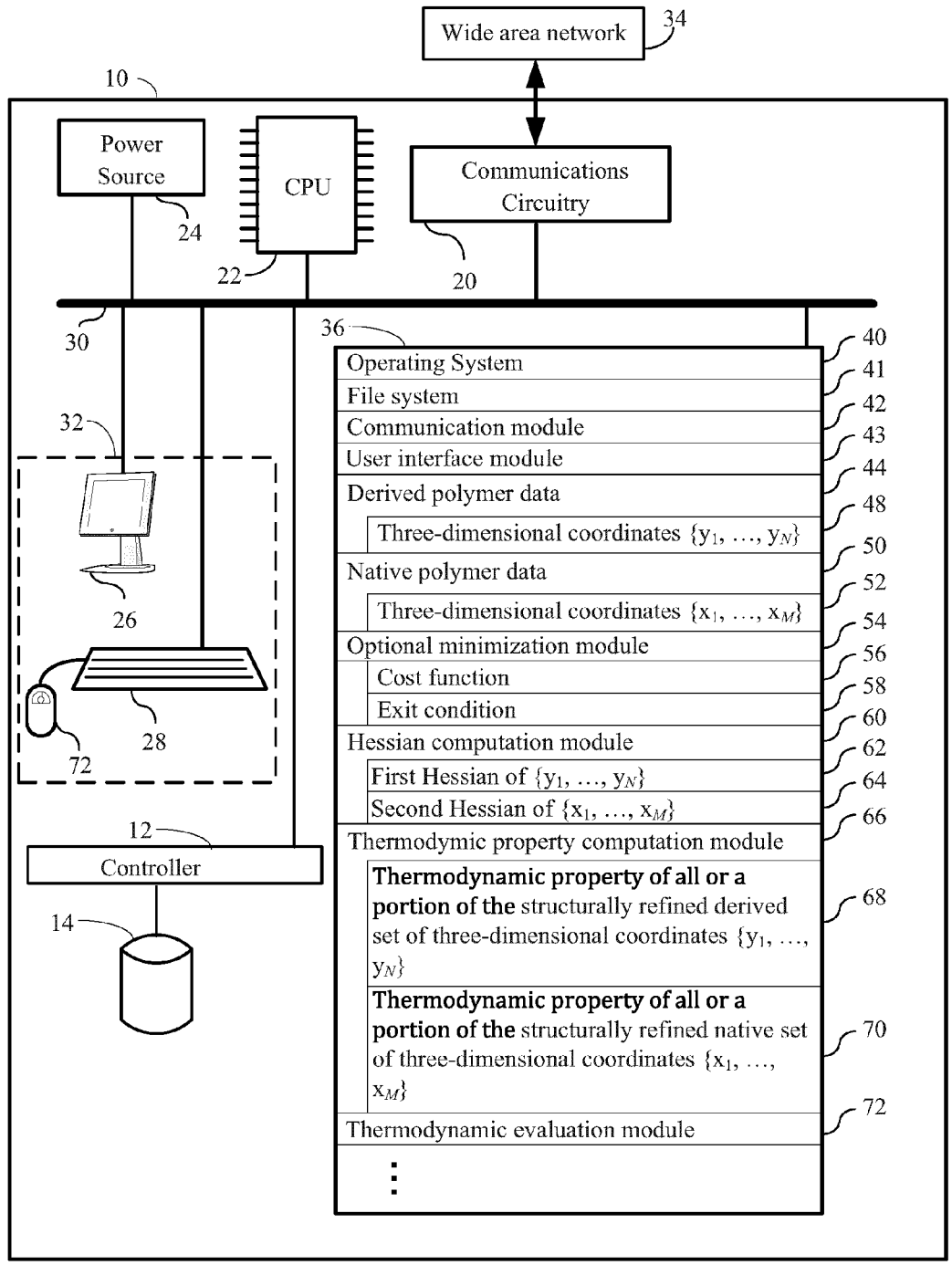
FIG. 1 is a block diagram illustrating a system for identifying a thermodynamic effect of an atomic replacement, insertion or deletion in a polymer, according to some embodiments.

FIG. 1 is a block diagram illustrating a computer according to some embodiments. The computer 10 typically includes one or more processing units (CPU's, sometimes called processors) 22 for executing programs (e.g., programs stored in memory 36), one or more network or other communications interfaces 20, memory 36, a user interface 32, which includes one or more input devices (such as a keyboard 28, mouse 72, touch screen, keypads, etc.) and one or more output devices such as a display device 26, and one or more communication buses 30 for interconnecting these components. The communication buses 30 may include circuitry (sometimes called a chipset) that interconnects and controls communications between system components.

Memory 36 includes high-speed random access memory, such as DRAM, SRAM, DDR RAM or other random access solid state memory devices; and typically includes non-volatile memory, such as one or more magnetic disk storage devices, optical disk storage devices, flash memory devices, or other non-volatile solid state storage devices. Memory 36 optionally includes one or more storage devices remotely located from the CPU(s) 22. Memory 36, or alternately the non-volatile memory device(s) within memory 36, comprises a non-transitory computer readable storage medium. In some embodiments, the non-volatile components in memory 36 include one or more hard drives 14 controlled by one or more hard drive controllers 12. In some embodiments, memory 36 or the computer readable storage medium of memory 36 stores the following programs, modules and data structures, or a subset thereof:

- an operating system 40 that includes procedures for handling various basic system services and for performing hardware dependent tasks;
- a file system 41 for handling basic file I/O tasks;
- an optional communication module 42 that is used for connecting the computer 10 to other computers via the one or more communication interfaces 20 (wired or wireless) and one or more communication networks 34, such as the Internet, other wide area networks, local area networks, metropolitan area networks, and so on;
- an optional user interface module 43 that receives commands from the user via the input devices 28, 72, etc. and generates user interface objects in the display device 26;
- derived polymer data 44, including a derived set of three-dimensional coordinates $\{y_1, \ldots, y_N\}$ 48 for a derivation of a native polymer that, optionally, have been structurally refined;
- native polymer data 50, native set of three-dimensional coordinates $\{x_1, \ldots, x_M\}$ 52 for the native polymer that, optionally, have been structurally refined;

an optional minimization module 54 for refining the derived set of three-dimensional coordinates, or a portion thereof, and for refining the native set of three-dimensional coordinates, or a portion thereof, against a cost function 56 until an exit condition 58 is achieved;

a Hessian computation module 60 for computing a first Hessian 62 using all or a portion of the structurally refined derived set of three-dimensional coordinates $\{y_1, \ldots, y_N\}$ 48 and for computing a second Hessian 64 using all or a portion of the structurally refined native set of three-dimensional coordinates $\{x_1, \ldots, x_M\}$ 52;

a thermodynamic property computation module 66 for computing a thermodynamic property 68 of all or a portion of the structurally refined derived set of three-dimensional coordinates $\{y_1, \ldots, y_N\}$ 48 using the first Hessian and for computing a thermodynamic property 70 of all or a portion of the structurally refined native set of three-dimensional coordinates $\{x_1, \ldots, x_M\}$ 52 using the second Hessian; and a thermodynamic evaluation module 72 for comparing the thermodynamic properties of the native to derived polymers to determine an effect of a polymer atomic replacement, insertion or deletion (e.g., by taking a difference between a thermodynamic property of the derived and native polymers).

In some embodiments, the polymer under study is a protein, a polypeptide, a polynucleic acid, a polyribonucleic acid, a polysaccharide, or an assembly of any combination thereof. In some embodiments, the polymer under study comprises between 2 and 5,000 residues, between 20 and 50,000 residues, more than 30 residues, more than 50 residues, or more than 100 residues. In some embodiments the polymer under study has a molecular weight of 100 Daltons or more, 200 Daltons or more, 300 Daltons or more, 500 Daltons or more, 1000 Daltons or more, 5000 Daltons or more, 10,000 Daltons or more, 50,000 Daltons or more or 100,000 Daltons or more.

The derivation of the polymer under study is formed by incorporating the atomic replacement, insertion or deletion under study into the polymer and structurally refining the polymer to form a structurally refined derived set of three-dimensional coordinates $\{y_1, \ldots, y_N\}$ for a derivation of the polymer. This structural refinement is optionally performed by minimization module 54. Each respective $y_i$ in $\{y_1, \ldots, y_N\}$ represents the position of an atom in three-dimensional space. For example, in some embodiments, the complex molecule is a protein, and each $y_i$ in the set of $\{y_1, \ldots, y_N\}$ is the three-dimensional coordinates of an atom in the protein.

In some embodiments, the programs or modules identified above correspond to sets of instructions for performing a function described above. The sets of instructions can be executed by one or more processors (e.g., the CPUs 22). The above identified modules or programs (e.g., sets of instructions) need not be implemented as separate software programs, procedures or modules, and thus various subsets of these programs or modules may be combined or otherwise re-arranged in various embodiments. In some embodiments, memory 36 stores a subset of the modules and data structures identified above. Furthermore, memory 36 may store additional modules and data structures not described above.

Figure 2:
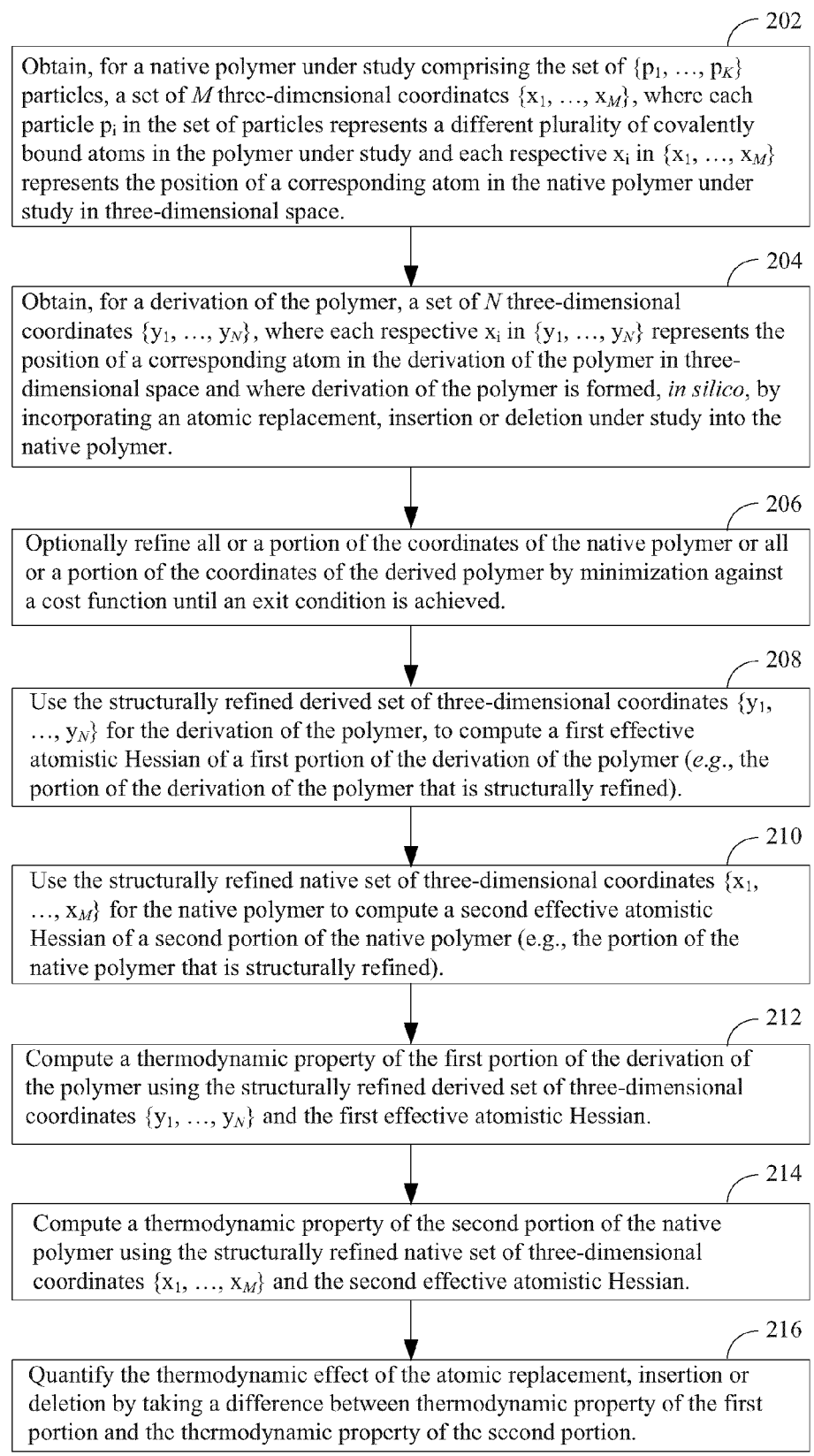
FIG. 2 illustrates a method for identifying a thermodynamic effect of an atomic replacement, insertion or deletion in a polymer, according to some embodiments.

Now that a system in accordance with the systems and methods of the present disclosure has been described, attention turns to FIG. 2 which illustrates an exemplary method in accordance with the present disclosure.

Step 202.

In step 202, a set of M three-dimensional coordinates $\{x_1, \ldots, x_M\}$ is obtained for a native polymer (polymer under study) comprising a set of $\{p_1, \ldots, p_K\}$ particles. Each particle $p_i$ in the set of $\{p_1, \ldots, p_K\}$ particles represents a different plurality of covalently bound atoms in the native polymer. In one example, the native polymer is a polynucleic acid and each particle $p_i$ in the set of $\{p_1, \ldots, p_K\}$ particles represents a nucleic acid residue in the polynucleic acid. In another example, the native polymer is a polyribonucleic acid and each particle $p_i$ in the set of $\{p_1, \ldots, p_K\}$ particles represents a ribonucleic acid residue in the polyribonucleic acid. In still another example, the native polymer is a polysaccharide and each particle $p_i$ in the set of $\{p_1, \ldots, p_K\}$ particles represents a monosaccharide unit or a disaccharide unit in the polysaccharide.

In still another example, the native polymer is a protein and each particle $p_i$ in the set of $\{p_1, \ldots, p_K\}$ particles represents a residue in the protein. In some such embodiments, each respective coordinate $x_i$ in $\{x_1, \ldots, x_M\}$ is the three-dimensional coordinates of a corresponding atom in the molecule under study in three-dimensional space. Here, M is a positive integer that represents the number of atoms in the native polymer. For instance, in some embodiments the native polymer comprises more than 100 atoms and, correspondingly, M is an integer greater than 100.

A polymer, such as those studied using the disclosed systems and methods, is a large molecule composed of repeating structural units. These repeating structural units are termed particles or residues interchangeably herein. In some embodiments, each particle $p_i$ in the set of $\{p_1, \ldots, p_K\}$ particles represents a single different residue in the native polymer. To illustrate, consider the case where the native comprises 100 residues. In this instance, the set of $\{p_1, \ldots, p_K\}$ comprises 100 particles, with each particle in $\{p_1, \ldots, p_K\}$ representing a different one of the 100 particles. In some embodiments the polymer is a protein is each particle is an amino acid residue.

In some embodiments, the native polymer is a natural material. In some embodiments, the native polymer is a synthetic material. In some embodiments, the native polymer is an elastomer, shellac, amber, natural or synthetic rubber, cellulose, Bakelite, nylon, polystyrene, polyethylene, polypropylene, or polyacrylonitrile, polyethylene glycol, or polysaccharide.

In some embodiments, the native polymer is a heteropolymer (copolymer). A copolymer is a polymer derived from two (or more) monomeric species, as opposed to a homopolymer where only one monomer is used. Copolymerization refers to methods used to chemically synthesize a copolymer. Examples of copolymers include, but are not limited to, ABS plastic, SBR, nitrile rubber, styrene-acrylonitrile, styrene-isoprene-styrene (SIS) and ethylene-vinyl acetate. Since a copolymer consists of at least two types of constituent units (also structural units, or particles), copolymers can be classified based on how these units are arranged along the chain. These include alternating copolymers with regular alternating A and B units. See, for example, Jenkins, 1996, "Glossary of Basic Terms in Polymer Science," Pure Appl. Chem. 68 (12): 2287-2311, which is hereby incorporated herein by reference in its entirety. Additional examples of copolymers are periodic copolymers with A and B units arranged in a repeating sequence (e.g. (A-B-A-B-B-A-A-A-A-B-B-B)$_n$). Additional examples of copolymers are statistical copolymers in which the sequence of monomer residues in the copolymer follows a statistical rule. If the probability of finding a given type monomer residue at a particular point in the chain is equal to the mole fraction of that monomer residue in the chain, then the polymer may be referred to as a truly random copolymer. See, for example, Painter, 1997, *Fundamentals of Polymer Science*, CRC Press, 1997, p 14, which is hereby incorporated by reference herein in its entirety. Still other examples of copolymers that may be evaluated using the disclosed systems and methods are block copolymers comprising two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively.

In some embodiments, the native polymer is in fact a plurality of polymers, where the respective polymers in the plurality of polymers do not all have the molecular weight. In some such embodiments, the polymers in the plurality of polymers fall into a weight range with a corresponding distribution of chain lengths. In some embodiments, the native polymer is a branched polymer molecule comprising a main chain with one or more substituent side chains or branches. Types of branched polymers include, but are not limited to, star polymers, comb polymers, brush polymers, dendronized polymers, ladders, and dendrimers. See, for example, Rubinstein et al., 2003, *Polymer physics*, Oxford; New York: Oxford University Press. p. 6, which is hereby incorporated by reference herein in its entirety.

In some embodiments, the native polymer is a polypeptide. As used herein, the term "polypeptide" means two or more amino acids or residues linked by a peptide bond. The terms "polypeptide" and "protein" are used interchangeably herein and include oligopeptides and peptides. An "amino acid," "residue" or "peptide" refers to any of the twenty standard structural units of proteins as known in the art, which include imino acids, such as proline and hydroxyproline. The designation of an amino acid isomer may include D, L, R and S. The definition of amino acid includes nonnatural amino acids. Thus, selenocysteine, pyrrolysine, lanthionine, 2-aminoisobutyric acid, gamma-aminobutyric acid, dehydroalanine, ornithine, citrulline and homocysteine are all considered amino acids. Other variants or analogs of the amino acids are known in the art. Thus, a polypeptide may include synthetic peptidomimetic structures such as peptoids. See Simon et al., 1992, Proceedings of the National Academy of Sciences USA, 89, 9367, which is hereby incorporated by reference herein in its entirety. See also Chin et al., 2003, Science 301, 964; and Chin et al., 2003, Chemistry & Biology 10, 511, each of which is incorporated by reference herein in its entirety.

The polypeptides evaluated in accordance with some embodiments of the disclosed systems and methods may also have any number of posttranslational modifications. Thus, a polypeptide includes those that are modified by acylation, alkylation, amidation, biotinylation, formylation, γ-carboxylation, glutamylation, glycosylation, glycylation, hydroxylation, iodination, isoprenylation, lipoylation, cofactor addition (for example, of a heme, flavin, metal, etc.), addition of nucleosides and their derivatives, oxidation, reduction, pegylation, phosphatidylinositol addition, phosphopantetheinylation, phosphorylation, pyroglutamate formation, racemization, addition of amino acids by tRNA (for example, arginylation), sulfation, selenoylation, ISGylation, SUMOylation, ubiquitination, chemical modifications (for example, citrullination and deamidation), and treatment with other enzymes (for example, proteases, phosphotases and kinases). Other types of posttranslational modifications are known in the art and are also included.

In some embodiments, the native polymer is an organometallic complex. An organometallic complex is chemical compound containing bonds between carbon and metal. In some instances, organometallic compounds are distinguished by the prefix "organo-" e.g. organopalladium compounds. Examples of such organometallic compounds include all Gilman reagents, which contain lithium and copper. Tetracarbonyl nickel, and ferrocene are examples of organometallic compounds containing transition metals. Other examples include organomagnesium compounds like iodo(methyl)magnesium MeMgI, diethylmagnesium ($Et_2Mg$), and all Grignard reagents; organolithium compounds such as n-butyllithium (n-BuLi), organozinc compounds such as diethylzinc ($Et_2Zn$) and chloro(ethoxycarbonylmethyl)zinc ($ClZ_nCH_2C(=O)OEt$); and organocopper compounds such as lithium dimethylcuprate ($Li^+[CuMe_2]^-$). In addition to the traditional metals, lanthanides, actinides, and semimetals, elements such as boron, silicon, arsenic, and selenium are considered form organometallic compounds, e.g. organoborane compounds such as triethylborane ($Et_3B$).

In some embodiments, the native polymer is a surfactant. Surfactants are compounds that lower the surface tension of a liquid, the interfacial tension between two liquids, or that between a liquid and a solid. Surfactants may act as detergents, wetting agents, emulsifiers, foaming agents, and dispersants. Surfactants are usually organic compounds that are amphiphilic, meaning they contain both hydrophobic groups (their tails) and hydrophilic groups (their heads). Therefore, a surfactant molecule contains both a water insoluble (or oil soluble) component and a water soluble component. Surfactant molecules will diffuse in water and adsorb at interfaces between air and water or at the interface between oil and water, in the case where water is mixed with oil. The insoluble hydrophobic group may extend out of the bulk water phase, into the air or into the oil phase, while the water soluble head group remains in the water phase. This alignment of surfactant molecules at the surface modifies the surface properties of water at the water/air or water/oil interface.

Examples of ionic surfactants include ionic surfactants such as anionic, cationic, or zwitterionic (ampoteric) surfactants. Anionic surfactants include (i) sulfates such as alkyl sulfates (e.g., ammonium lauryl sulfate, sodium lauryl sulfate), alkyl ether sulfates (e.g., sodium laureth sulfate, sodium myreth sulfate), (ii) sulfonates such as docusates (e.g., dioctyl sodium sulfosuccinate), sulfonate fluorosurfactants (e.g., perfluorooctanesulfonate and perfluorobutanesulfonate), and alkyl benzene sulfonates, (iii) phosphates such as alkyl aryl ether phosphate and alkyl ether phosphate, and (iv) carboxylates such as alkyl carboxylates (e.g., fatty acid salts (soaps) and sodium stearate), sodium lauroyl sarcosinate, and carboxylate fluorosurfactants (e.g., perfluorononanoate, perfluorooctanoate, etc.). Cationic surfactants include pH-dependent primary, secondary, or tertiary amines and permanently charged quaternary ammonium cations. Examples of quaternary ammonium cations include alkyltrimethylammonium salts (e.g., cetyl trimethylammonium bromide, cetyl trimethylammonium chloride), cetylpyridinium chloride (CPC), benzalkonium chloride (BAC), benzethonium chloride (BZT), 5-bromo-5-nitro-1,3-dioxane, dimethyldioctadecylammonium chloride, and dioctadecyldimethylammonium bromide (DODAB). Zwitterionic surfactants include sulfonates such as CHAPS (3-[(3-Cholamidopropyl)dimethylammonio]-1-propanesulfonate)

and sultaines such as cocamidopropyl hydroxysultaine. Zwitterionic surfactants also include carboxylates and phosphates.

Nonionic surfactants include fatty alcohols such as cetyl alcohol, stearyl alcohol, cetostearyl alcohol, and oleyl alcohol. Nonionic surfactants also include polyoxyethylene glycol alkyl ethers (e.g., octaethylene glycol monododecyl ether, pentaethylene glycol monododecyl ether), polyoxypropylene glycol alkyl ethers, glucoside alkyl ethers (decyl glucoside, lauryl glucoside, octyl glucoside, etc.), polyoxyethylene glycol octylphenol ethers ($C_8H_{17}$—($C_6H_4$)—(O—$C_2H_4$)$_{1-25}$—OH), polyoxyethylene glycol alkylphenol ethers ($C_9H_{19}$—($C_6H_4$)—(O—$C_2H_4$)$_{1-25}$—OH, glycerol alkyl esters (e.g., glyceryl laurate), polyoxyethylene glycol sorbitan alkyl esters, sorbitan alkyl esters, cocamide MEA, cocamide DEA, dodecyldimethylamine oxideblock copolymers of polyethylene glycol and polypropylene glycol (poloxamers), and polyethoxylated tallow amine. In some embodiments, the polymer under study is a reverse micelle, or liposome.

In some embodiments, the native polymer is a fullerene. A fullerene is any molecule composed entirely of carbon, in the form of a hollow sphere, ellipsoid or tube. Spherical fullerenes are also called buckyballs, and they resemble the balls used in association football. Cylindrical ones are called carbon nanotubes or buckytubes. Fullerenes are similar in structure to graphite, which is composed of stacked graphene sheets of linked hexagonal rings; but they may also contain pentagonal (or sometimes heptagonal) rings.

In some embodiments, the set of M three-dimensional coordinates $\{x_1, \ldots, x_M\}$ for the native polymer are obtained by x-ray crystallography, nuclear magnetic resonance spectroscopic techniques, or electron microscopy. In some embodiments, the set of M three-dimensional coordinates $\{x_1, \ldots, x_M\}$ is obtained by modeling (e.g., molecular dynamics simulations).

In some embodiments, the native polymer includes two different types of polymers, such as a nucleic acid bound to a polypeptide. In some embodiments, the native polymer includes two polypeptides bound to each other. In some embodiments, the native polymer under study includes one or more metal ions (e.g. a metalloproteinase with a one or more zinc atoms) and/or is bound to one or more organic small molecules (e.g., an inhibitor). In such instances, the metal ions and or the organic small molecules may be represented as one or more additional particles $p_i$ in the set of $\{p_1, \ldots, p_K\}$ particles representing the native polymer.

In some embodiments, there are ten or more, twenty or more, thirty or more, fifty or more, one hundred or more, between one hundred and one thousand, or less than 500 particles in the native polymer.

There is no requirement that each atom in a particle $p_i$ be covalently bound to each other atom in a particle in the native polymer. More typically, each atom in a particle $p_i$ is covalently bound to at least one other atom in the particle, as is the typical case in an amino acid residue in a polypeptide. Moreover, typically, for each respective particle $p_i$ in the set of $\{p_1, \ldots, p_K\}$ particles, there is at least one atom in the respective particle $p_i$ that is covalently bound to an atom in another particle in the set of $\{p_1, \ldots, p_K\}$ particles.

Step 204.

In step 204 there is obtained, for a derivation of the native polymer, a set of N three-dimensional coordinates $\{y_1, \ldots, y_N\}$, where each respective $y_i$ in $\{y_1, \ldots, y_N\}$ represents the position of a corresponding atom in the derivation of the native polymer. The derivation of the polymer is formed, in silico, by incorporating an atomic replacement, insertion or deletion under study into the native polymer. In some embodiments, the polymer is a protein and the atomic replacement, insertion or deletion is a mutation of one or more residues in the derivation of the polymer relative to the native polymer. In some embodiments, the native polymer is a protein and the derivation of the polymer differs from the native polymer by the insertion or deletion of one or more residues at one or more locations in the polymer.

Step 206.

In some embodiments, the N three-dimensional coordinates $\{y_1, \ldots, y_N\}$ for the native polymer and the set of M three-dimensional coordinates $\{x_1, \ldots, x_M\}$ for the native polymer respectively obtained in steps 202 and 204 are already structurally refined. In some embodiments either the native or the derived set of coordinates, or both, are refined using optional minimization module 54 which makes use of a cost function 56 with one or more exit conditions 58.

In some embodiments, a region of the derivation of the polymer that encompasses the site of the atomic replacement, insertion or deletion is refined in step 206 while all other portions of the derivation of the polymer are held fixed. In some embodiments, the region of the native polymer that corresponds to this refinement region of the derivation of the polymer is refined in step 206 while all other portions of the derivation of the polymer are held fixed. In some embodiments, the region of the polymer that encompasses the site of the atomic replacement, insertion or deletion consists of the atoms of the polymer that are within a threshold distance of the atomic replacement, insertion or deletion is refined while all other regions are held fixed. In some embodiments, the distance threshold is "X" Angstroms, where "X" is any value between 5 and 50 (e.g., 5, 10, 15, 20, 25, 30, 35, 40, 45, 50, etc.).

By way of an example, consider a native polymer that is a one hundred residue protein with a leucine at residue position 50. The atomic replacement is the replacement of this leucine with a phenylalanine, and those atoms in $\{y_1, \ldots, y_N\}$ that are within ten Angstroms of the $C_{alpha}$ carbon of phenylalanine 50 are selected for refinement by minimization module 54 while all other atoms of the derivation of the polymer are held fixed.

By way of another example, the native polymer is a one hundred residue protein with a leucine at residue position 50, the atomic replacement is the replacement of this leucine with a phenylalanine, and those atoms in $\{y_1, \ldots, y_N\}$ that are in a residue that has at least one atom within ten Angstroms of the $C_{alpha}$ carbon of phenylalanine 50 are selected for refinement by minimization module 54 while other atoms of the derivation of the polymer are held fixed.

By way of still another example, the native polymer is a one hundred residue protein with a leucine at residue position 50 and a proline at position 60, the atomic replacement is the replacement of the leucine at position 50 with a phenylalanine and the replacement of proline at position 60 with an alanine, and those atoms in $\{y_1, \ldots, y_N\}$ that are within ten Angstroms of the $C_{alpha}$ carbon of phenylalanine 50 or the $C_{alpha}$ carbon of alanine 60 are selected for refinement by minimization module 54 while all other atoms of the derivation of the polymer are held fixed.

By way of yet another example, the native polymer is a one hundred residue protein with a leucine at residue position 50 and a proline at position 60, the atomic replacement is the replacement of the leucine at position 60 with a phenylalanine and the replacement of the proline at position 60 with an alanine, and those atoms in $\{y_1, \ldots, y_N\}$ that are in a residue that has at least one atom within ten Angstroms of the $C_{alpha}$ carbon of phenylalanine 50 or the $C_{alpha}$ carbon of alanine 60 are selected for refinement by minimization module 54 while other atoms of the derivation of the polymer are held fixed.

The above examples make it clear that, to form the derivation of the polymer from the native polymer, at least one residue of the native polymer is identified, in silico, and is optionally replaced with a different residue. In fact, more than one residue can be identified. In practice, one or more residues of the native polymer are identified in the initial structural coordinates $\{x_1, \ldots, x_M\}$. The identified one or more residues are either replaced with different residues or deleted. In some embodiments, one or more residues in the native polymer are deleted when forming the derivation of the polymer in silico. Alternatively or additionally, a position between a first particle and a second particle in the native polymer is identified, where the first particle and the second particle share a covalent bond, and one or more particles are inserted, in silico, between the first and second particle. In some such embodiments the native polymer is a protein the first and second particles are amino acid residues, and the one or more particles that are inserted are each amino acid residues. In some embodiments any combination of atomic replacement, insertion or deletion of atoms, including whole residues, into the native polymer is performed in order to arrive at the derivation of the polymer.

In one embodiment, a single residue of the native polymer is identified, and replaced with a different residue, and the region of the derivation of the polymer that is selected for refinement is defined as a sphere having a predetermined radius, where the sphere is centered either on a particular atom of the mutated residue (e.g., $C_\alpha$ carbon in the case of proteins) or the center of mass of the identified residue. In some embodiments, the predetermined radius is five Angstroms or more, 10 Angstroms or more, or 20 Angstroms or more. For example, in one embodiment, the native polymer is a protein comprising 200 residues and an alanine at position 100 (i.e., the $100^{th}$ residues of the 200 residue protein) that is found in the polymer 44 is changed to a tyrosine (i.e., A100W). Then, the region of the derivation of the polymer that is selected for refinement is defined based on the position of A100W. In some embodiments, the region of the polymer is the $C_{alpha}$ carbon or a designated main chain atom of residue 100 either before or after the side chain has been replaced.

In some embodiments, more than two residues are identified and the region of the polymer that is refined in fact is more than two regions. For example, in some embodiments, the polymer is a protein, two different residues are mutated, and the region of the derivation of the polymer that is refined comprises (i) a first sphere having a predetermined radius that is centered on the $C_{alpha}$ carbon of the first mutated residue and (ii) a second sphere having a predetermined radius that is centered on the $C_{alpha}$ carbon of the second mutated residue. Depending on how close the two substitutions are, the spheres may or may not overlap. In alternative embodiments, more than two residues are identified, and optionally mutated, and the region that is selected for refinement is a single contiguous region.

In some embodiments, two, three, four, five, or more than five residues of the native polymer are mutated in silico to form the derivation of the polymer. In some embodiments, this plurality of residues consists of three residues. There is no requirement that these residues be contiguous within the native polymer. In some of the foregoing embodiments, the region of the derivation of the polymer containing mutations relative to the native polymer is a single region that is defined as a sphere having a predetermined radius, where the sphere is centered at a center of mass of the plurality of identified residues either before or after optional substitution. In some embodiments, the predetermined radius is five Angstroms or more, 10 Angstroms or more, or 20 Angstroms or more. For example, in one embodiment, the native polymer is a protein comprising 200 residues and an alanine at position 100 (i.e., the $100^{th}$ residue of the 200 residue protein) that is found in the native polymer is changed to a tyrosine (i.e., A100W) and a leucine at position 102 of the native polymer is changed to an isoleucine (i.e., L102I) in order to form the derivation of the polymer in silico. Then, the region of the derivation of the polymer 49 is defined based on the positions of A100W and L102I. In some embodiments, the region of the derivation of the polymer is the center of mass of A100W and L102I either before or after the mutations have been made. It will be appreciated that this center of mass may fall outside the Van der Waals space occupied by residues 100 and 102.

Now that there has been discussion of what regions of the polymers are refined, examples of refinement in accordance with step 206 are provided. In these examples, the one or more regions of a polymer selected for refinement are represented by the cost function 56. In some embodiments, the cost function 56 estimates the potential energy of the selected portions of the native polymer (when refining the selected portions of the native polymer) or the selected portions of the derivation of the polymer (when refining the selected portions of the derivation of the polymer). In such embodiments, the cost function 56 includes terms relating to the various relationships between the parts of the polymer. Thus, in some embodiments the cost function includes terms that account for energy due to, for example, bond length, bond angle, and dihedral angles, as well as nonbonding interactions such as Coulombic and Lennard-Jones interactions within the polymer being refined. In some embodiments, the cost function 56 further includes cross or other higher order terms.

In some embodiments, the cost function 56 is minimized using a quasi-Newton method, such as the Broyden-Fletcher-Goldfarb-Shanno (BFGS). In quasi-Newton methods, the Hessian matrix of second derivatives need not be evaluated directly. Instead, the Hessian matrix is approximated using rank-one updates specified by gradient evaluations (or approximate gradient evaluations). Quasi-Newton methods are a generalization of the secant method to find the root of the first derivative for multidimensional problems. In multi-dimensions the secant equation does not specify a unique solution, and quasi-Newton methods differ in how they constrain the solution.

In some embodiments, the cost function 56 is minimized using a random walk method, such as simulated annealing ("SA"), that does not require derivatives. In some such embodiments, a "hill-climbing method", such as steepest decent or BFGS, is used. In some embodiments, simulated annealing is used to refine the cost function 56 rather than hill-climbing methods.

As noted above, the cost function is minimized until an exit condition is achieved. In some instances, the exit condition is determined by the method by which the cost function is minimized. For example, Berinde, 1997, Novi SAD J. Math, 27, 19-26, which is incorporated herein by reference, outlines some exit conditions for Newton's method. In some embodiments, the exit condition is achieved when a predetermined maximum number of iterations of the refinement algorithm used to refine the cost function have been computed. In some embodiments, the predetermined maximum number of iterations is ten iterations, twenty iterations, one hundred iterations or one thousand iterations.

In some embodiments the selected regions of the native polymer or the derivation of the polymer are refined using a minimization algorithm and a suitable force field, such as the MSI CHARMM force field, variants thereof, and equivalents thereof. See Brooks, 1983, J. Comp. Chem., 4, 187-217, and Schleyer, 1998, CHARMM: The Energy Function and Its Parameterization with an Overview of the Program, in The Encyclopedia of Computational Chemistry, 1:271-277 eds., John Wiley & Sons, Chichester, each of which is hereby incorporated by reference.

Steps 208 and 210.

In the steps leading to step 208, the coordinates for a native polymer and the coordinates for a derivation of the polymer have been obtained. The native polymer and the derivation of the polymer differ from each other by some combination of atomic replacements, insertions, or deletions, or any combination thereof, as described above. Furthermore, in typical embodiments, at least some of the coordinates of both the native polymer and the derivation of the polymer have been refined as described above. It will be appreciated that there is no requirement that the native polymer correspond to, or be, a naturally occurring polymer. As used herein, the term "native" is used as a label to uniquely specify one of the sets of coordinates that are being used to examine the thermodynamic properties of some combination of atomic replacements, insertions, and/or deletions in a polymer.

The partial refinement of the native polymer and the partial refinement of the derivation of the polymer allow for the computation of the full atomistic Hessian of the refinement zone of the native polymer, and the full atomistic Hessian of the refinement zone of the derivation of the polymer. In typical embodiments, portions of the native polymer and the derivation of the polymer outside of the refinement zones are not optimized and the degrees of freedom of elements outside the refinement zone are not included in the atomic Hessian of the refinement zones.

As discussed above, in some embodiments, what is sought is an effective atomistic Hessian matrix of only those coordinates $\{y_1, \ldots, y_N\}$ that were structurally refined (e.g., the refinement zone). In some embodiments, what is sought is an effective atomistic Hessian matrix of only those coordinates $\{y_1, \ldots, y_N\}$ that were structurally refined (e.g., the refinement zone), other than the atoms that were altered by the atomic replacement, insertion or deletion. In some embodiments what is sought is a first effective atomistic Hessian matrix of a first subset of interest of those coordinates $\{y_1, \ldots, y_N\}$ of the derivation of the polymer that were structurally refined but were not altered in the atomic replacement, insertion or deletion. This first subset of interest comprises the first portion of the derivation of the polymer. What is further sought is a second effective atomistic Hessian matrix of a second subset of interest consisting of those coordinates in $\{x_1, \ldots, x_M\}$ of the native polymer that exactly correspond to the atoms that are in the first subset of interest of the derivation of the polymer. This second subset of interest consists of the second portion of the native polymer. The first and second effective Hessian matrices are computed in steps 208 and 210 respectively. To illustrate, consider the case in which the native polymer is a 100 residue protein and the derivation of the polymer is identical to the native polymer with the exception that an alanine at position 50 is mutated to a phenylalanine (denoted A50F). Moreover, a 15 Angstrom sphere around this mutation is refined in the derivation of the polymer and an equivalent sphere is refined in the native polymer structure using the techniques referenced above. In this example, a first effective atomistic Hessian is computed using the atoms in the 15 Angstrom refinement sphere of the derivation of the polymer, other than the atoms in the mutated phenylalanine at position 50. The other portions of the derivation of the polymer are treated as background by the first effective atomistic Hessian. In step 210, a second effective atomistic Hessian is computed using the atoms in the 15 Angstrom refinement sphere of the native polymer, other than the atoms in the alanine at position 50. The other portions of the native polymer are treated as background by the second effective atomistic Hessian.

Effective atomistic Hessians can be constructed using vibrational subsystem analysis conducted by reviewing the potential energy of the refinement zone of the native polymer or the refinement zone of the derivation of the polymer under study, expressed as:

$$2E_{pot} = x^T H x = [x_s^T x_e^T] H \begin{bmatrix} x_s \\ x_e \end{bmatrix} = x_s^T H_{ss} x_s + x_s^T H_{se} x_e + x_e^T H_{ee} x_e.$$

For the derivation of the polymer, vector $x_s$ is defined as the displacements of the atoms in the first subset of interest (first portion of the derivation of the polymer), while vector $x_e$ is defined as the displacement of the atoms in the refinement zone of the derivation of the polymer that are not in the first subset of interest. For the native polymer, vector $x_s$ is defined as the displacements of the atoms in the second subset of interest, while vector $x_e$ is defined as the displacement of the atoms in the refinement zone of the derivation of the polymer that are not in the second subset of interest. The full Hessian of the refinement zone defined as $$H = \begin{bmatrix} H_{ss} & H_{se} \\ H_{es} & H_{ee} \end{bmatrix}$$

where, $H_{ss}$, $H_{se}$, and $H_{ee}$ are respectively the Hessian of the subset of interest, the Hessian coupling the subset of interest to the remainder of the refinement zone, and the Hessian of atoms in the refinement zone that are not in the subset of interest. Thus, for the derivation of the polymer, $H_{ss}$, $H_{se}$, and $H_{ee}$ are respectively the Hessian of the first subset of interest, the Hessian coupling the first subset of interest to the remainder of the refinement zone of the derivation of the polymer, and the Hessian of atoms in the refinement zone of the derivation of the polymer that are not in the first subset of interest. For the native polymer, $H_{ss}$, $H_{se}$, and $H_{ee}$ are respectively the Hessian of the second subset of interest, the Hessian coupling the second subset of interest to the remainder of the refinement zone of the native polymer, and the Hessian of atoms in the refinement zone of the native that are not in the second subset of interest.

The coordinates $x_e$, are separated from coordinates $x_s$ by setting $$\frac{\partial E}{\partial x_e} = 0$$

as a constraint, which leads to $$e_x^0 = -H_{ee}^{-1} H_{es} x_s,$$

which further leads to the redefinition of the potential using an effective Hessian ($H_{ss}^{eff}$)

$$2E_{pot} = x_s^T \cdot H_{ss}^{eff} x_s = x_s^T (H_{ss} - H_{se} H_{ee}^{-1} H_{es}) x_s.$$

In this way, the potential energy of the refinement zone is made a function of the coordinates in the subset of interest only, and is described using the effective Hessian $H_{ss}^{eff}$. This is advantageous because the energy term $x_s^T H_{ss}^{eff} x_s$ does not contain any of the degrees of freedom of the atoms of the atomic replacement, insertion or deletion, assuming the subset of interest was chosen to exclude the atoms in the atomic replacement, insertion or deletion. Consequently, quantities derived from this energy can be directly compared between the native polymer and the derivation of the polymer (or derived polymers created by altering a common native polymer in different ways). The effective Hessian also approximately accounts for the coupling between the degrees of freedom in the subset of interest and the degrees of freedom that are in the refinement zone, but are not in the subset of interest. Additionally $H_{ss}^{eff}$ is smaller than H, thereby reducing the computational complexity involved in computing thermodynamic quantities.

In step 210, a structurally refined native set of three-dimensional coordinates $\{x_1, \ldots, x_M\}$ for the native polymer is used to compute a second effective atomistic Hessian of a second portion of the native polymer. In some embodiments, the atoms in the second portion of the native polymer exactly correspond to the atoms of the first portion of the derivation of the polymer, with only those atoms that have been structurally refined included in the respective first and second portions, and with all atoms participating in the atomic replacement, insertion or deletion in the polymer excluded from the first or second portions.

There is no requirement in the instant methods for the regions that are refined to exactly correspond to the regions for which an effective Hessian is computed. To illustrate, consider the case in which the native polymer is a 100 residue protein and the derivation of the polymer is identical to the native polymer with the exception that an alanine at position 50 is mutated to a phenylalanine (denoted A50F). Moreover, a 30 Angstrom sphere around this mutation is refined in the derivation of the polymer and an equivalent sphere is refined in the native structure using the techniques referenced above. In this example, a first effective atomistic Hessian is computed using the atoms in a 15 Angstrom sphere around the mutation in the derivation of the polymer, other than the atoms in the mutated phenylalanine at position 50. The other portions of the derivation of the polymer are treated as background by the first effective atomistic Hessian. In step 210, a second effective atomistic Hessian is computed using the atoms in a corresponding 15 Angstrom refinement sphere of the native polymer, other than the atoms in the alanine at position 50. The other portions of the native polymer are treated as background by the second effective atomistic Hessian.

Step 212.

In step 212, a thermodynamic property of the first portion of the derivation of the polymer is computed using the structurally refined derived set of three-dimensional coordinates $\{y_1, \ldots, y_N\}$ and the first effective atomistic Hessian. In some embodiments, the thermodynamic property of the first portion of the derivation of the polymer is entropy, average energy, average enthalpy, free energy or heat capacity of the first portion. As an example, the entropy of a region with an effective atomic Hessian $H^{eff}$ is computed by first finding all the non-zero eigenvalues $\{\lambda_i\}$ of the mass weighted effective Hessian $M^{-1/2} H^{eff} M^{-1/2}$. Here the diagonal of M contains the masses of the atoms corresponding to the degrees of freedom included in the effective Hessian. With the eigenvalues computed, the entropy is then:

$$N k_B + k_B \sum_{i=1}^{N} \ln\left[\frac{k_B T}{\hbar \lambda_i^{1/2}}\right],$$

where $k_B$ is the Boltzmann's constant, N is the number of degrees of freedom in the effective Hessian, T is a temperature, usually taken to be 300K, and $\hbar$ is the reduced Planck's constant.

Step 214.

In step 214, a thermodynamic property of the second portion of the native polymer is compute using the structurally refined native set of three-dimensional coordinates $\{x_1, \ldots, x_M\}$ and the second effective atomistic Hessian. In some embodiments, the thermodynamic property of the first portion of the derivation of the polymer is entropy, average energy, average enthalpy, free energy or heat capacity of the first portion.

Step 216.

In step 216, the thermodynamic effect of the atomic replacement, insertion or deletion is quantified by taking a difference between the thermodynamic property of the first portion and the thermodynamic property of the second portion.

In some embodiments, the first portion, from the structurally refined derived set of three-dimensional coordinates $\{y_1, \ldots, y_N\}$ does not include the atoms that are part of the atomic replacement, insertion or deletion in a polymer. Further, the second portion, from the native set of three-dimensional coordinates $\{x_1, \ldots, y_M\}$ does not include the atoms that are part of the atomic replacement, insertion or deletion in a polymer. In such embodiments, the number of degrees of freedom in the first portion and the second portion are exactly the same even though one represents the native polymer and the other represents the derivation of the polymer. In such embodiments, the thermodynamic property computed using the effective atomistic Hessians of the first and second portions can be exactly compared without normalizing for a difference in degree in freedom. This is particularly beneficial when the thermodynamic property being computed is entropy.

However, the instant systems and methods do not require the exact partitioning of the first and second portions such that they have the same number of degrees of freedom. For instance, they may have different degrees of freedom which may be taken into account when comparing computed thermodynamic values for the first and second portions. In one such approach, a structurally refined derived set of three-dimensional coordinates $\{y_1, \ldots, y_N\}$ is used for a derivation of the polymer. The derivation of the polymer is formed by incorporating the atomic replacement, insertion or deletion into the polymer, to compute a first effective atomistic Hessian of the derivation of the polymer. In this instance, the first effective atomistic Hessian may be a Hessian derived through a vibrational subsystem analysis, or may be the full atomistic Hessian of all the coordinates $\{y_1, \ldots, y_N\}$. Each respective $y_i$ in $\{y_1, \ldots, y_N\}$ is a three dimensional coordinate for an atom in a first plurality of atoms in the derivation of the polymer. A structurally refined native set of three-dimensional coordinates $\{x_1, \ldots, x_M\}$ for the native polymer is used to compute a second effective atomistic Hessian of the native polymer, where each respective $x_i$ in $\{x_1, \ldots, x_M\}$ is a three dimensional coordinate for an atom in a second plurality of atoms in the native polymer, and where an identity of at least one $y_i$ in $\{y_1, \ldots, y_N\}$ is different than an identity of the corresponding $x_i$ in $\{x_1, \ldots, x_M\}$ or N is different than M. In this instance, the second effective atomistic Hessian may be a Hessian derived through a vibrational subsystem analysis or may be the full atomistic Hessian of all the coordinates $\{x_1, \ldots, x_M\}$. An unnormalized thermodynamic property of the derivation of the polymer is computed using the structurally refined derived set of three-dimensional coordinates and the first effective atomistic Hessian. An unnormalized thermodynamic property of the native polymer is computed using the structurally refined native set of three-dimensional coordinates and the second effective atomistic Hessian. The unnormalized thermodynamic property of the derivation of the polymer and the unnormalized thermodynamic property of the native polymer are respectively normalized by taking into account a difference in a number of degrees of freedom of $\{y_1, \ldots, y_N\}$ relative to $\{x_1, \ldots, x_M\}$, thereby identifying a thermodynamic effect of the atomic replacement, insertion or deletion in the polymer.

The methods illustrated in FIG. 2 may be governed by instructions that are stored, in a non-transitory manner, in a computer readable storage medium and that are executed by at least one processor of at least one server. Each of the operations shown in FIG. 2 may correspond to instructions stored in a non-transitory computer memory or computer readable storage medium. In various implementations, the non-transitory computer readable storage medium includes a magnetic or optical disk storage device, solid state storage devices such as Flash memory, or other non-volatile memory device or devices. The computer readable instructions stored on the non-transitory computer readable storage medium may be in source code, assembly language code, object code, or other instruction format that is interpreted and/or executable by one or more processors.

EXAMPLES

Example 1

Figure 3:
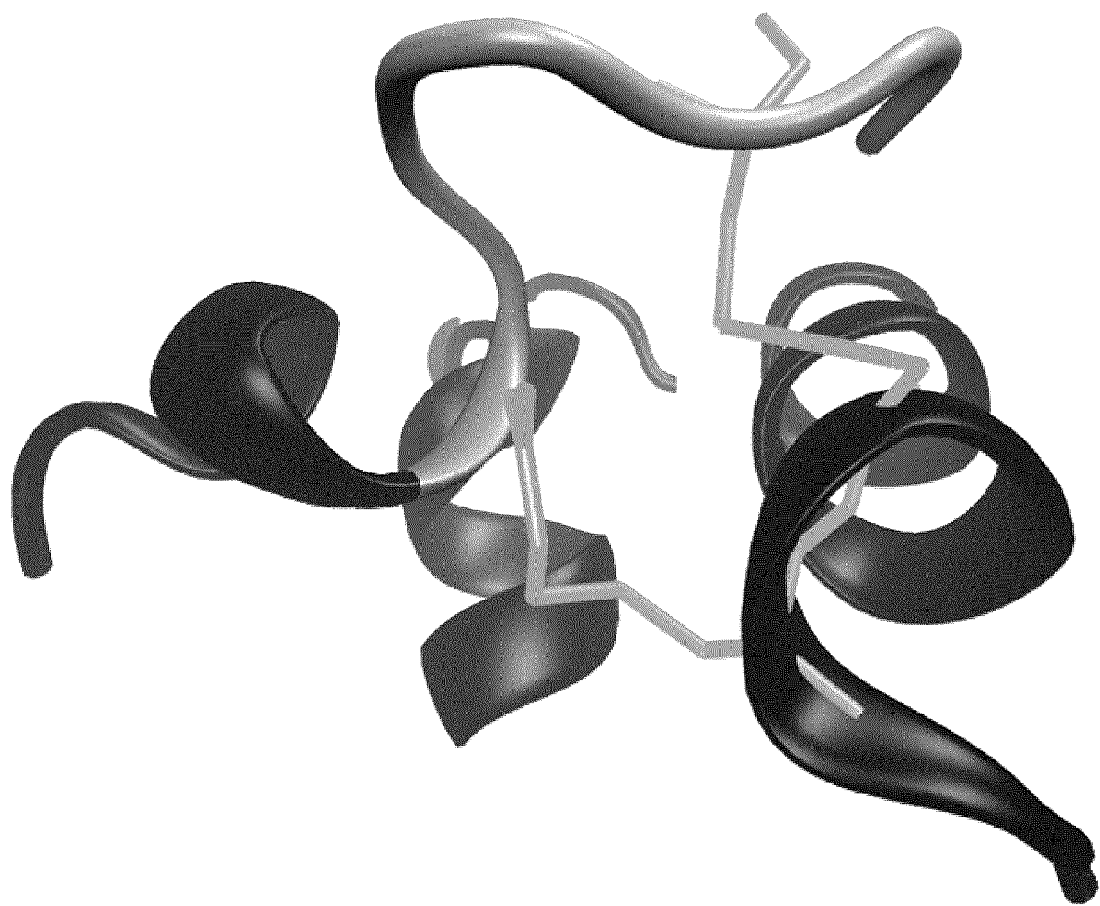
FIG. 3 illustrates the refinement zone in a protein, used to compute the difference in the entropy of a loop resulting from a set of mutations, according to some embodiments.

In this example, the ability of the systems and methods of the present disclosure to compute the entropy of an arbitrary predetermined subset of degrees of freedom in a protein is demonstrated. The example makes use of an antibody-antigen complex crystal structure (PDB Accession Record 3HFM), here referred to as the wild-type structure. A mutant structure was produced by mutating the residues Y/5.ARG, Y/6.CYS, and Y/127.CYS in the wild-type structure to alanine residues. A refinement region was then defined on the basis of the coordinates of the wild-type structure. The refinement region for the wild-type structure contained all the atoms of any residue with at least one heavy atom (i.e. an atom other than a hydrogen atom) that had a distance less than or equal to 8 Å from any heavy atom of residues Y/124 to Y/129 inclusive in the wild-type structure. The refinement region in the wild-type structure is shown in FIG. 3, with the side-chains of residues Y/5, Y/6 and Y/127 displayed as thin lines. The refinement region for the mutant structure contained the same atoms as the wild-type refinement region, with the exception of the atoms of the mutated residues Y/5.ARG, Y/6.CYS, and Y/127.CYS. In the refinement region of the mutant structure, the atoms of these residues were replaced by the atoms of residues Y/5.ALA, Y/6.ALA, and Y/127.ALA.

The coordinates of the refinement regions so defined were then optimized using an implementation of the limited-memory Broyden-Fletcher-Goldfarb-Shanno method (LB-FGS), and the AMBER atomistic potential energy function. The LBFGS method is described in Byrd et al., 1995, "A limited memory algorithm for bound constrained optimization," *SIAM Journal on Scientific and Statistical Computing* 16, 1190, which is hereby incorporated by reference herein in its entirety. Background on the AMBER potential is found in Ponder and Case, 2003, "Force fields for protein simulations," *Adv. Prot. Chem.* 66, 27, which is hereby incorporated by reference herein in its entirety. After minimization of the refinement regions of the wild-type structure and the mutant structure, atomistic Hessians of the wild-type refinement region ($H_{wt}$), and the mutant refinement region ($H_{mut}$) were computed. A vibrational subsystem analysis was then applied to $H_{wt}$ to compute an effective Hessian ($H_1$), which contained the degrees of freedom of the backbone atoms belonging to residues Y/124 to Y/129 inclusive in the wild-type structure. In FIG. 3 the backbone of residues Y/124 to Y/129 are displayed in light gray.

A vibrational subsystem analysis was also applied to $H_{mut}$ to compute an effective Hessian ($H_2$), which also contained the degrees of freedom of the backbone atoms belonging to residues Y/124 to Y/129. The effective Hessians included the backbone degrees of freedom of the Y/127 residue that was mutated from CYS to ALA however, as only backbone degrees of freedom are included, the effective Hessians $H_1$ and $H_2$ contained the same number of degrees of freedom. Applying the equation $$Nk_B + k_B \sum_{i=1}^{N} \ln\left[\frac{k_B T}{\hbar \lambda_i^{1/2}}\right],$$

previously described above to $H_1$, produced a numeric estimate (1700 kcal/mol K) of the entropy of the backbone atoms of residues Y/124 to Y/129 in the wild type structure. The application of this same equation to $H_2$ produced an estimate (1726 kcal/mol K) of the entropy of these atoms in the mutant structure. The difference between these two entropy estimates was approximately 26 kcal/mol K. This difference indicates that mutating Y/5.ARG, Y/6.CYS and Y/127.CYS to alanine residues produces an increase in the entropy of the backbone coordinates of Y/124 to Y/129. This increase in entropy is consistent with an increase in the conformational flexibility of the loop backbone.

Example 2

This example describes a typical use of the systems and methods of the present disclosure in which the entropy of the local environment about a mutation is computed. The mutation is performed in a crystal structure of an antibody FAB region (PDB Accession Record 1JPT), and consisted of mutating residue A/427 from a valine to an alanine. A refinement region was defined on the basis of the coordinates of the wild-type structure. This region contained all atoms of any residue with at least one heavy atom (i.e. an atom other than a hydrogen atom) that had a distance less than or equal to 8 Å from any heavy atom of A/427.VAL. The refinement region for the mutant structure contained the same atoms as the wild-type refinement region, with the exception of the atoms of the mutated residue A/427.VAL, which were replaced by the atoms of an alanine residue. The coordinates of the refinement regions so defined were then optimized using an implementation of the limited-memory Broyden-Fletcher-Goldfarb-Shanno method (LBFGS), and the AMBER atomistic potential energy function. After minimization of the refinement regions of the wild-type structure and the mutant structure, atomistic Hessians of the wild-type refinement region ($H_{wt}$), and the mutant refinement region ($H_{mut}$) were computed. A vibrational subsystem analysis was then applied to $H_{wt}$ to compute an effective Hessian ($H_1$), which contained the degrees of freedom of all atoms in the wild-type refinement region, excluding those atoms composing the side-chain of residue A/427.VAL. A vibrational subsystem analysis was also applied to $H_{mut}$ to compute an effective Hessian ($H_2$), which contained the degrees of freedom of all atoms in the mutant refinement region excluding the atoms composing the side-chain of residue A/427.ALA. As the only sequence difference between the wild-type and mutant proteins occurs at residue A/427, the effective Hessians $H_1$ and $H_2$ include the same degrees of freedom. The same equation used in Example 1 was applied to the effective Hessian $H_1$ to compute the entropy of the environment around residue A/427.VAL in the wild-type structure, yielding a value of approximately 14232 kcal/mol K. This same equation was also applied to the effective Hessian $H_2$, to compute the entropy for the environment around residue A/427.ALA in the mutant structure, yielding a value of approximately 14266 kcal/mol K. The difference between these two entropy values (34 kcal/mol K) indicates that the mutation of A/427 from a valine to an alanine residue increased the entropy of the local environment. This increase in entropy is consistent with an increase in the conformational flexibility of the region near residue A/427.

CONCLUSION

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the exemplary configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first contact could be termed a second contact, and, similarly, a second contact could be termed a first contact, which changing the meaning of the description, so long as all occurrences of the "first contact" are renamed consistently and all occurrences of the second contact are renamed consistently. The first contact and the second contact are both contacts, but they are not the same contact.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A method of identifying a thermodynamic effect of an atomic replacement, insertion or deletion in a native polymer, the method comprising:
    at a computer system having one or more processors and memory storing one or more programs to be executed by the one of more processors:
    (A) using a derived set of three-dimensional coordinates for a derivation of the native polymer, wherein the derived set of three-dimensional coordinates that form the derivation of the native polymer comprises incorporation of an atomic replacement of one or more atoms that are in the native polymer, or an insertion or deletion a of one or more residues relative to the sequence of residues of the native polymer, to compute a first effective atomistic Hessian of a first portion of the derived set of three-dimensional coordinates that represents a first portion of the derivation of the native polymer, wherein each respective three-dimensional coordinate in the derived set of three-dimensional coordinates is a three dimensional coordinate for an atom in a first plurality of atoms in the derivation of the native polymer;

(B) using a native set of three-dimensional coordinates for the native polymer to compute a second effective atomistic Hessian of a second portion of the native set of three-dimensional coordinates that represents a second portion of the native polymer, wherein each respective native three-dimensional coordinate in the native set of three-dimensional coordinates is a three dimensional coordinate for an atom in a second plurality of atoms in the native polymer;

(C) computing a thermodynamic property of the first portion of the derivation of the native polymer using the derived set of three-dimensional coordinates and the first effective atomistic Hessian; and (D) computing a thermodynamic property of the second portion of the native polymer using the native set of three-dimensional coordinates and the second effective atomistic Hessian.

2. The method of claim 1, wherein an identity of each atom in the first portion of the derived set of three-dimensional coordinates is identical to the corresponding atom in the second portion of the native set of three-dimensional coordinates.

3. The method of claim 1, wherein the thermodynamic effect of the atomic replacement of the one or more atoms in the native polymer, or the insertion or deletion of one or more residues relative to the sequence of residues of the native polymer is quantified by taking a difference between the thermodynamic property of the first portion of the derived set of three-dimensional coordinates and the thermodynamic property of the second portion of the native set of three-dimensional coordinates.

4. The method of claim 1, wherein the native polymer is a protein and the atomic replacement of the one or more atoms in the native polymer, or the insertion or deletion of one or more residues relative to the sequence of residues of the native polymer is a mutation of one or more residues in the derivation of the native polymer relative to the primary sequence of residues of the native polymer.

5. The method of claim 1, wherein the native polymer is a protein and wherein the derivation of the native polymer differs from the native polymer by the insertion or deletion of one or more residues in the sequence of the native polymer.

6. The method of claim 1, wherein the thermodynamic property of the first portion of the derivation of the native polymer is entropy, average energy, average enthalpy, free energy or heat capacity.

7. The method of claim 1, wherein the first portion of the derived set of three-dimensional coordinates consists of those atoms in the first plurality of atoms within a distance threshold of the location of the atomic replacement of the one or more atoms that are in the native polymer, or the insertion or deletion of the one or more residues relative to the sequence of residues of the native polymer.

8. The method of claim 1, wherein the native polymer is a protein, a polypeptide, a polynucleic acid, a polyribonucleic acid, a polysaccharide, or an assembly of any combination thereof.

9. The method of claim 1, wherein
the derived set of three-dimensional coordinates is prepared prior to computing the first effective atomistic Hessian by structurally refining a region encompassing the first portion while holding the other portions of the derived set of three-dimensional coordinates fixed; and the native set of three-dimensional coordinates is prepared prior to computing the second effective atomistic Hessian by structurally refining a region encompassing the second portion of the native polymer while holding the other portions of the native set of three-dimensional coordinates fixed.

10. The method of claim 1, wherein
the derived set of three-dimensional coordinates is obtained by structurally refining a first refinement zone of the derivation of the native polymer, the first refinement zone including the atoms in the atomic replacement of the one or more atoms that are in the native polymer, or the insertion or deletion of the one or more residues relative to the sequence of residues of the native polymer;

the using (A) partitions atoms in the first refinement zone into a first partition and a second partition, wherein the first partition consists of the atoms in the refinement zone that are in the atomic replacement of one or more atoms that are in the native polymer, or the insertion or deletion of one or more residues relative to the sequence of residues of the native polymer and the second partition consists of all or a subset of those atoms in the first refinement zone other than those atoms in the first partition, and wherein the second partition is deemed to be the first portion of the derivation of the native polymer, the using (B) structurally refines a second refinement zone of the native set of three-dimensional coordinates, the second refinement zone corresponding to the first refinement zone;

the using (B) partitions atoms in the second refinement zone into a third partition and a fourth partition, wherein the fourth partition consists of those atoms in the native set of three-dimensional coordinates that are equivalent to those atoms in the second partition, and wherein the fourth partition is deemed to be the second portion of the native polymer.

11. The method of claim 10, wherein
an atomistic Hessian of the first refinement zone is decomposed using a vibrational subsystem analysis to produce the first effective atomistic Hessian, and the entropy of the first portion is computed from the first effective atomistic Hessian; and a second atomistic Hessian of the second refinement zone is decomposed using a vibrational subsystem analysis to produce the second effective Hessian, and the entropy of the second portion is computed from the second effective Hessian.

12. The method of claim 10, wherein the native polymer is a protein, and the atomic replacement of the one or more atoms that are in the native polymer, or the insertion or deletion of the one or more residues relative to the sequence of residues of the native polymer is a mutated residue.

13. The method of claim 10, wherein the refinement zone consists of those atoms in the first plurality of atoms within a distance threshold of the location of the atomic replacement of the one or more atoms that are in the native polymer, or the insertion or deletion of the one or more residues that are in the sequence of residues of the native polymer.

14. The method of claim 1, wherein
the using (A) structurally refines a first refinement zone in the derived set of three-dimensional coordinates prior to computing the second effective atomistic Hessian, the first refinement zone including the atoms in the atomic replacement of the one or more atoms that are in the native polymer, or the insertion or deletion of the one or more residues relative to the sequence of residues of the native polymer;

the using (A) further partitions atoms in the first refinement zone into a first partition and a second partition, wherein the atoms in the second partition consists of all or a subset of the atoms in the refinement zone other than those atoms in the atomic replacement of the one or more atoms that are in the native polymer, or the insertion or deletion of the one or more residues relative to the sequence of residues of the native polymer, the atoms in the first partition consists of those atoms in the first refinement zone that are not in the second partition, and wherein the using (B) structurally refines the native set of three-dimensional coordinates prior to computing the second effective atomistic Hessian by refining a second refinement zone of the native polymer, the second refinement zone corresponding to the first refinement zone but differing by those atoms participating in the atomic replacement of the one or more atoms that are in the native polymer, or the insertion or deletion of the one or more residues relative to the sequence of residues of the native polymer; and the using (B) further partitions atoms in the second refinement zone into a third partition and a fourth partition, wherein the identity of the atoms in the fourth partition exactly correspond to their counterparts in the second partition and wherein the second portion of the native polymer consists of the atoms in the fourth petition.

15. The method of claim 14, wherein the first effective atomistic Hessian of the first refinement zone is decomposed using a vibrational subsystem analysis to produce a first effective Hessian matrix, and the entropy of the first portion is computed from the first effective Hessian matrix; and the second effective atomistic Hessian of the second refinement zone is decomposed using a vibrational subsystem analysis to produce a second effective Hessian matrix, and the entropy of the second portion is computed from the second effective Hessian matrix.

16. The method of claim 14, wherein the native polymer is a protein, and the atomic replacement of the one or more atoms that are in the native polymer, or the insertion or deletion of the one or more residues that are in the sequence of residues of the native polymer is a mutated residue.

17. The method of claim 14, wherein the first partition consists of those atoms in the first plurality of atoms within a distance threshold of the location of the atomic replacement of the one or more atoms that are in the native polymer, or the insertion or deletion of the one or more residues relative to the sequence of residues of the native polymer.

18. A method of identifying a thermodynamic effect of an atomic replacement, insertion or deletion in a native polymer, the method comprising:

at a computer system having one or more processors and memory storing one or more programs to be executed by the one of more processors:

(A) using a derived set of three-dimensional coordinates for a derivation of the native polymer, wherein the derived set of three-dimensional coordinates that form the derivation of the native polymer comprises the incorporation of an atomic replacement of one or more atoms that are in the native polymer, or the insertion or deletion of one or more residues relative to the sequence of residues of the native polymer, to compute a first effective atomistic Hessian of the derivation of the native polymer, wherein each respective three-dimensional coordinate in the derived set of three-dimensional coordinates is a three dimensional coordinate for an atom in a first plurality of atoms in the derivation of the native polymer;

(B) using a native set of three-dimensional coordinates for the native polymer to compute a second effective atomistic Hessian of the native polymer, wherein each respective native three-dimensional coordinate in the native set of three-dimensional coordinates is a three dimensional coordinate for an atom in a second plurality of atoms in the native polymer;

(C) computing an unnormalized thermodynamic property of the derivation of the native polymer using the derived set of three-dimensional coordinates and the first effective atomistic Hessian;

(D) computing an unnormalized thermodynamic property of the native polymer using the structurally refined native set of three-dimensional coordinates and the second effective atomistic Hessian; and (E) normalizing the unnormalized thermodynamic property of the derivation of the native polymer and the unnormalized thermodynamic property of the native polymer by taking into account a difference in a number of degrees of freedom of the derived set of three-dimensional coordinates relative to the native set of three-dimensional coordinates, thereby identifying a thermodynamic effect of the atomic replacement, insertion or deletion in the polymer.

19. The method of claim 18, wherein the native polymer is a protein and the atomic replacement of the one or more atoms in the native polymer, or the insertion or deletion of one or more residues relative to the sequence of residues of the native polymer is a mutation of one or more residues in the derivation of the native polymer relative to the sequence of residues of the native polymer.

20. The method of claim 18, wherein the native polymer is a protein and wherein the derivation of the native polymer differs from the native polymer by the insertion or deletion of one or more residues in the sequence of the native polymer.

21. The method of claim 18, wherein the derived set of three-dimensional coordinates is prepared prior to computing the first effective atomistic Hessian by structurally refining a first portion of the derived set of three-dimensional coordinates about a location of the replacement of the one or more atoms that are in the native polymer, or the insertion or deletion of one or more residues relative to the sequence of residues of the native polymer while holding the other portions of the derived set of three-dimensional coordinates fixed; and the native set of three-dimensional coordinates is prepared prior to computing the second effective atomistic Hessian by structurally refining a second portion of the native native set of three-dimensional coordinates while holding the other portions of the native set of three-dimensional coordinates fixed, the second portion being the part of the native polymer corresponding to the first portion of the derived set of three-dimensional coordinates.

22. The method of claim 21, wherein the first region consists of those atoms in the first plurality of atoms within a distance threshold of the location of the replacement of the one or more atoms that are in the native polymer, or the insertion or deletion of the one or more residues relative to the sequence of residues of the native polymer.

23. The method of claim 18, wherein the native polymer is a protein, a polypeptide, a polynucleic acid, a polyribonucleic acid, a polysaccharide, or an assembly of any combination thereof.

24. A computer system for identifying a thermodynamic effect of an atomic replacement, insertion or deletion in a native polymer, the computer system comprising at least one processor and memory storing at least one program for execution by the at least one processor, the memory further comprising instructions for:
(A) using a derived set of three-dimensional coordinates for a derivation of the native polymer, wherein the derived set of three-dimensional coordinates that form the derivation of the native polymer comprises the incorporation of an atomic replacement of one or more atoms that are in the native polymer, or the insertion or deletion of one or more residues relative to the sequence of residues of the native polymer, to compute a first effective atomistic Hessian of a first portion of the derivation of the native polymer, wherein each respective three-dimensional coordinate in the derived set of three-dimensional coordinates is a three dimensional coordinate for an atom in a first plurality of atoms in the derivation of the native polymer;
(B) using a native set of three-dimensional coordinates for the native polymer to compute a second effective atomistic Hessian of a second portion of the native polymer, wherein each respective native three-dimensional coordinate in the native set of three-dimensional coordinates is a three dimensional coordinate for an atom in a second plurality of atoms in the native version of the polymer;
(C) computing a thermodynamic property of the first portion of the derivation of the native polymer using the derived set of three-dimensional coordinates and the first effective atomistic Hessian; and
(D) computing a thermodynamic property of the second portion of the native polymer using the native set of three-dimensional coordinates and the second effective atomistic Hessian.

25. The computer system of claim 24 wherein an identity of each atom in the first portion of the derived set of three-dimensional coordinates is identical to the corresponding atom in the second portion of the native three-dimensional coordinates.

26. A non-transitory computer readable storage medium storing a computational module for identifying a thermodynamic effect of an atomic replacement, insertion or deletion in a native polymer, the computational module comprising instructions for:
(A) using a derived set of three-dimensional coordinates for a derivation of the native polymer, wherein the derived set of three-dimensional coordinates that form the derivation of the native polymer comprises incorporation of an atomic replacement of one or more atoms that are in the native polymer, or an insertion or deletion of one or more residues relative to the sequence of residues of the native polymer, to compute a first effective atomistic Hessian of a first portion of the derived set of three-dimensional coordinates that represents a first portion of the derivation of the native polymer, wherein each respective three-dimensional coordinate in the derived set of three-dimensional coordinates is a three dimensional coordinate for an atom in a first plurality of atoms in the derivation of the native polymer;
(B) using a native set of three-dimensional coordinates for the native polymer to compute a second effective atomistic Hessian of a second portion of the native set of three-dimensional coordinates that represents a second portion of the native polymer, wherein each respective native three-dimensional coordinate in the native set of three-dimensional coordinates is a three dimensional coordinate for an atom in a second plurality of atoms in the native polymer;
(C) computing a thermodynamic property of the first portion of the derivation of the native polymer using the derived set of three-dimensional coordinates and the first effective atomistic Hessian; and
(D) computing a thermodynamic property of the second portion of the native polymer using the native set of three-dimensional coordinates and the second effective atomistic Hessian.

27. The non-transitory computer readable storage medium of claim 26 wherein an identity of each atom in the first portion of the derived set of three-dimensional coordinates is identical to the corresponding atom in the second portion of the native three-dimensional coordinates.

* * * * *